US012582792B2

(12) United States Patent
O'Connor

(10) Patent No.: US 12,582,792 B2
(45) Date of Patent: ***Mar. 24, 2026

(54) RESPIRATORY SYSTEM AND MASK INTERFACE

(71) Applicant: Fisher & Paykel Healthcare Limited, Auckland (NZ)

(72) Inventor: James Patrick O'Connor, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 692 days.

This patent is subject to a terminal disclaimer.

(21) Appl. No.: 17/842,349

(22) Filed: Jun. 16, 2022

(65) Prior Publication Data

US 2023/0113791 A1     Apr. 13, 2023

Related U.S. Application Data

(63) Continuation of application No. 16/335,651, filed as application No. PCT/NZ2017/050125 on Sep. 26, 2017, now Pat. No. 11,389,612.

(60) Provisional application No. 62/399,605, filed on Sep. 26, 2016.

(51) Int. Cl.
*A61M 16/06* (2006.01)
*A61M 16/08* (2006.01)

(52) U.S. Cl.
CPC ........ *A61M 16/0683* (2013.01); *A61M 16/06* (2013.01); *A61M 16/0616* (2014.02); *A61M 16/0666* (2013.01); *A61M 16/0875* (2013.01); *A61M 2205/0216* (2013.01)

(58) Field of Classification Search
CPC .... A41D 13/11; A41D 13/1146; A61B 5/087; A61B 5/6803; A61D 7/04; A61M 16/06; A61M 16/0616; A61M 16/0666; A61M 16/0683; A61M 16/0875; A61M 16/208; A61M 2205/0216; A61M 2205/42; A61M 2205/7536; A61M 2206/14; A61M 2210/0618; A61M 2230/42; A62B 18/02; A62B 18/025; A62B 23/02; A62B 23/025
See application file for complete search history.

(56) References Cited

U.S. PATENT DOCUMENTS

| | | | | |
|---|---|---|---|---|
| 3,505,998 A | * | 4/1970 | Brown | A61D 7/04 128/207.11 |
| 3,521,630 A | * | 7/1970 | Westberg | A62B 23/025 55/528 |
| 4,098,270 A | * | 7/1978 | Dolby | A62B 18/02 128/206.29 |
| 4,354,488 A | * | 10/1982 | Bartos | A61M 16/06 128/205.25 |
| 4,630,604 A | * | 12/1986 | Montesi | A41D 13/1146 128/206.17 |
| 4,873,972 A | * | 10/1989 | Magidson | A62B 18/025 128/206.15 |
| 11,389,612 B2 | * | 7/2022 | O'Connor | A61M 16/0875 |

(Continued)

*Primary Examiner* — Annette Dixon
(74) *Attorney, Agent, or Firm* — VIA LLP

(57) ABSTRACT

A mask interface for a respiratory mask, in which the mask interface comprises a resilient mask housing at least partially formed from a textile and being configured to deform under pressure from an external force, such as when being pressed against a pillow, and to substantially return to its original shape either automatically or by manipulation by a user.

25 Claims, 7 Drawing Sheets

(56)                    References Cited

U.S. PATENT DOCUMENTS

| | | | |
|---|---|---|---|
| 2002/0162556 A1* | 11/2002 | Smith .................... | A61B 5/087 |
| | | | 128/207.12 |
| 2003/0205231 A1* | 11/2003 | Shigematsu ........... | A41D 13/11 |
| | | | 128/206.24 |
| 2005/0098183 A1* | 5/2005 | Nash .................... | A61M 16/06 |
| | | | 128/206.27 |
| 2007/0131229 A1* | 6/2007 | Madaus ................ | A61M 16/06 |
| | | | 128/206.21 |

* cited by examiner

RESPIRATORY SYSTEM AND MASK INTERFACE

BACKGROUND

Technical Field

The present disclosure generally relates to a respiratory system for the delivery of respiratory therapy to a user. More particularly, the present disclosure relates to a respiratory mask and a mask interface for use in a respiratory system.

Description of the Related Art

Respiratory masks and mask interfaces are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnoea (OSA), a condition in which a user's airway intermittently collapses, during sleep, preventing the user from breathing for a period of time. The cessation of breathing, or apnoea, results in the user awakening. Repetitive and frequent apnoeas may result in the user rarely achieving a full and restorative night's sleep.

CPAP therapy involves the delivery of a supply of continuous positive air pressure to the airway of the user via a respiratory mask. The continuous positive pressure acts as a splint within the user's airway, which secures the airway in an open position such that the user's breathing and sleep are not interrupted.

Respiratory masks typically comprise a mask interface and a headgear, wherein the mask interface is configured to deliver the supply of continuous positive air pressure to the user's airway via a seal or cushion that forms an airtight seal in or around the user's nose and/or mouth. The mask interface includes a seal or cushion that is held in place on the user's face by the headgear. In order to maintain an airtight seal the headgear should provide support to the mask interface such that it is held in a stable position relative to the user's face during use. Respiratory masks are available in a range of styles including full-face, nasal, direct nasal and oral masks, which create an airtight seal with the nose and/or mouth. Such respiratory masks may also be used to deliver NIV and other breathing treatment therapies.

Traditional mask interfaces may present several disadvantages. One disadvantage relates to the substantially rigid structure of the mask interface. Because most mask interfaces are substantially rigid in structure, users who wear respiratory masks with these mask interfaces often find that their ability to change sleeping positions is restricted, due to the rigid mask interface coming into contact with their pillow or other bedding. For example, a user may not be able to comfortably lie on their side when wearing a traditional full-face mask interface, as a result of the substantially rigid mask interface contacting the pillow. Contact between the mask interface and the pillow may hold the user's head at an uncomfortable angle; cause increased pressure points that lead to discomfort and in some cases skin damage; or cause the seal between the mask interface and the user's face to be broken, resulting in air leaks and loss of therapy.

Another disadvantage of traditional mask interfaces is that most CPAP mask interfaces on the market currently have a clinical appearance. Such an appearance may not be appealing for users to wear in a bedroom setting and may discourage users from wearing their mask and receiving effective breathing treatment therapy.

Some fully textile/fabric mask interfaces are available on the market. These textile masks may help avoid the sleep position difficulties that can arise with a rigid mask interface and may be designed to look less clinical in appearance. However, the overall lack of structure in existing textile mask interfaces can make them more difficult to use. The lack of structure also means that these types of mask interfaces are prone to collapsing on themselves when not in use. When a mask is in a collapsed configuration, such as after being placed in storage, the shape of the mask distorts, which can make it difficult for a user to understand how to reshape and apply the mask for a correct fit.

BRIEF SUMMARY

The systems and devices described herein have innovative aspects, no single one of which is indispensable or solely responsible for their desirable attributes. Without limiting the scope of the claims, some of the advantageous features will now be summarized.

In broad terms, the invention relates to a respiratory mask interface having a traditional silicone seal in combination with a resilient housing that is capable of deforming when it comes into contact with a sufficiently deforming external force (such as pressure from pressing against a pillow for example) and returning to its original form either automatically or by manipulation by a user. The invention also relates to a respiratory mask comprising such a compliant and resilient mask interface. In addition, the invention relates to a respiratory system for delivering breathing gas to a user and comprising a respiratory mask or mask interface according to the invention.

In a first aspect, the invention provides a mask interface for delivering breathing gas to a user, wherein the mask interface comprises:

a seal comprising a gas inlet configured to seal against the user's face; and a 3-dimensional mask housing directly or indirectly attached to the seal, wherein the mask housing comprises at least one gas inlet and wherein at least a portion of the mask housing is formed from fabric and comprises a first flexible, resilient support structure configured to at least partially retain the 3-dimensional shape of the mask housing Preferably, the seal is formed of silicone. The seal may also comprise a rolling bridge, wherein the seal comprises an upper portion configured to roll over onto an outer surface of the seal and/or the mask housing and/or the frame of the mask interface, as described in WO2012/140514, which is incorporated herein by reference. To assist with the rolling of the upper portion, the upper portion can have a varying thickness or a varying stiffness. To reduce the prevalence of ballooning in the upper portion and to provide enhanced structure in the upper portion, a reinforcing component or components, such as a band, can be positioned along at least a portion of the upper portion. The band extends along at least a portion of the upper portion of the seal. The upper portion of the mask comprises an apex when viewed from the front. The apex can be defined as a tip, a top or an angular summit of the mask seal, which apex is positioned in proximity to the nose of the user when in use.

The band and the stiffer region (e.g., a region of thicker cross section) adjacent to the region of reduced stiffness help to initiate rolling of the region of reduced stiffness. In other words, a controlled buckling of the region of reduced stiffness occurs with the assistance of the adjacent stiffer portions. In some configurations, the region of reduced stiffness is bounded by a first boundary and a second boundary, wherein the first boundary and the second boundary have an increased stiffness relative, to the region of reduced stiffness. In the illustrated configuration, for example, the first boundary is defined by or alongside the hand. The second boundary can be defined by or alongside an edge of the mask housing. In some configurations, the second boundary can be defined along a portion of the seal positioned between the mask housing and the region of reduced stiffness.

As the upper portion of the seal is displaced about a hinge axis, the roll increases in size. In other words, as the first boundary initially moves toward the second boundary, a roll is formed in the seal. As the first boundary continues to move toward the second boundary, the roll, continues to increase in site. Thus, the roll defined in the upper portion starts at nothing and progressively increases during displacement of the upper portion as shown in dashed lines. Preferably, the rolling between the first boundary and the second boundary creates a single bend or inflection between the first boundary and the second boundary.

In an embodiment, the mask interface comprises a first upper portion comprising a first wall and a second wall converging to an apex, the apex being positioned in use in proximity to the nose of a user; a lower portion being connected to and positioned below the first upper portion. The mask interface also comprises a face contacting flange defined at least in part by the first upper portion and the lower portion and a hinge axis (H) extending laterally across the mask interface, wherein the first upper portion is positioned vertically higher than the hinge axis (H). A first boundary extends along at least a portion of the first wall and along at least a portion of the second wall, the first boundary comprising a first end and a second end, both ends being spaced away from the hinge axis (H) toward the apex. The mask interface also comprises a radius R defined between the hinge axis (H) and the apex and a second upper portion positioned distally from the first upper portion in a direction away from the face contacting flange. The second upper portion comprises an arc length defined along an upper extremity of a surface of the second upper portion, the arc length forming a second boundary. A radius r is defined between the hinge axis (H) and an uppermost point of the arc length. The radius R is different than the radius r. At least a portion of a first outer surface of the first upper portion is configured to roll so as to overlie or underlie at least a portion of a second outer surface of the second upper portion when the first boundary is moved toward the second boundary.

In an embodiment, the mask interface comprises a first upper portion comprising a first wall and a second wall converging to an apex, the apex being positioned in use in proximity to the nose of a user. A lower portion is connected to and positioned below the first upper portion. A face contacting flange is defined at least in part by the first upper portion and the lower portion. A first boundary extends along at least a portion of the first wall and along at least a portion of the second wall. A second upper portion is positioned distally from the first upper portion in a direction away from the face contacting flange, the second upper portion comprising an arc length defined along an upper extremity of a surface of the second upper portion. The arc length forms a second boundary. The first upper portion further comprises a region of reduced stiffness positioned between the first and second boundaries, wherein the region of reduced stiffness is configured to roll to allow pivoting of at least a portion of the first upper portion relative to the second upper portion when the first boundary is moved toward the second boundary. The region of reduced stiffness is bounded by the first and second boundaries and the first and second boundaries having an increased stiffness relative to the region of reduced stiffness.

In an embodiment, the mask interface comprises a first upper portion comprising a first wall and a second wall converging to an apex. The apex is positioned in use in proximity to the nose of a user. A hinge axis (H) extends laterally across the mask interface and the first upper portion is positioned vertically higher than the hinge axis. A band extends along at least a portion of the first wall and along at least a portion of the second wall, the band comprising a first end and a second end, both ends being spaced away from the hinge axis (H) toward the apex. The band forms a first boundary. A radius R is defined between the hinge axis (H) and the apex. A second upper portion is positioned distally from the first upper portion in a direction away from a face contacting surface. The second upper portion comprises an arc length defined along an upper extremity of the surface of the second upper portion, the arc length forming a second boundary. A radius r is defined between the hinge axis (H) and an uppermost point of the arc length. The radius R is different than the radius r. At least a portion of a first outer surface of the first upper portion is configured to roll so as to overlie or underlie at least a portion of a second outer surface of the second upper portion when the first boundary is moved toward the second boundary. In an embodiment, the seal comprises a seal of flexible material, the seal having a first side and a second side, the first side of the seal being shaped to approximately match the contours of a user's face and in use substantially seal against a user's face, the second side attached to a clip. The clip comprises a bridging portion spanning outwards from the perimeter or periphery of the mask housing to space at least a portion of the second side of the seal outwards from the perimeter or periphery of the mask housing. The mask interface also comprises an inner cushion located between the bridging portion of the clip and the first side of the seal. The clip comprises a channel in the bridging portion. A first side of the inner cushion in use supports the first side of the seal, and a second side of the inner cushion is received in the channel.

In an embodiment, the seal comprises a first wall and a second wall converging to an apex, the apex being positioned in use in proximity to the nose of a user. The seal also comprises a face contacting flange and a hinge axis (H) extending laterally across the patient interface. An upper portion of the mask seal is positioned vertically higher than the hinge axis (H). A band extends along at least a portion of the first wall and along at least a portion of the second wall, the band comprising a first end and a second end, both ends being spaced away from the hinge axis (H) toward the apex. The band forms a first boundary. A radius R is defined between the hinge axis (H) and the apex. A mask seal clip is positioned distally from the mask seal in a direction away from the face contacting flange. An arc length is defined along an upper extremity of the surface of the mask seal clip. The arc length forms a second boundary, and a radius r is defined between the hinge axis (H) and an uppermost point of the arc length. The radius R is different than the radius r. At least a portion of a first outer surface of the mask seal is configured to roll so as to overlie or underlie at least a portion of a second outer surface of the mask seal clip when the first boundary is moved toward the second boundary In one form, the mask housing is fully formed from a textile. For example, the housing may comprise a single sheet of fabric comprising at least one seam or fold to form the 3-dimensional shape of the mask housing. Alternatively, the housing may comprise multiple pieces of fabric joined together by one or more seams to form a 3-dimensional shape.

Preferably, the fabric is airtight.

In one form, an airtight coating or layer is provided on an internal surface of at least the fabric portion of the mask housing.

In one form, the respiratory mask further comprises a frame comprising a gas inlet and being configured to attach to the seal and mask housing, so that the gas inlet of the frame substantially forms a fluid flow path with the gas inlets of the seal and mask housing.

Optionally, the frame forms a ring-like structure. In one form, the frame is located at or near an outer peripheral edge of the mask housing and is configured to provide a substantially rigid connection by which the mask housing may be connected to the seal.

Preferably, the frame is made from a polycarbonate, or other rigid or semi-rigid plastic.

In one form, the frame is over-moulded to the mask housing and the seal is over-moulded to the frame.

In one form, the frame comprises a support structure comprising one or more resilient support members that extend from the frame to support the 3-dimensional shape of the mask housing. Optionally, the support members are formed from the same material as the frame. In one form, the support members are co-moulded with the mask housing.

In one form, the first support structure of the mask housing is configured to at least partially deform under a sufficient deforming external force and to substantially return to its original shape after the force is removed. Preferably, the first support structure is configured to substantially return to its original shape automatically after the force is removed. Alternatively, the first support structure is configured to substantially return to its original shape under manipulation by a user after the deforming force is removed.

In one form, the first support structure is located on an interior surface of the mask housing.

In one form, the first support structure is integrally formed with the mask housing.

In another form, the first support structure is located on an exterior surface of the mask housing and is attached to the mask housing.

In one form, the first support structure comprises a resilient support layer applied to interior and/or exterior surfaces of the fabric portion of the mask housing to increase the thickness of one or more regions of the housing. The support layer may be applied near outer edges of the mask housing and/or along sides of the mask housing to increase the thickness of these regions. Preferably, the support layer comprises an elastomer. For example, the support layer may comprise a vinyl or silicone lining.

In one form, the first support structure comprises a skeleton structure comprising a plurality of resilient support members. Preferably, the structural support comprises a plurality of resilient or semi-resilient filaments. The filaments may be plastic filaments or metal wires. Optionally, the support members are located on an interior surface of the mask housing to form an internal skeleton support structure. In another form, the support members are integrally formed with at least one fabric portion of the mask housing. In yet another form, the support members are located on an exterior surface of the mask housing and are attached to the mask housing to provide structural support.

In another form, the first support structure comprises a ridge that is provided in a fabric portion of the mask housing. The ridge may comprise at least one fold line or seam along which the mask housing will naturally fold when squashed. Optionally, the ridge extends from a substantially central point at a central region of the mask housing to a substantially central point near an upper edge of the mask housing.

In one form, the mask housing is formed from multiple pieces of fabric joined by one or more seams, and wherein each seam is configured to form a ridge that provides structural support to the mask housing.

Optionally, the mask interface is configured for use with a CPAP machine.

Also disclosed herein is a mask interface for delivering breathing gas to a user. The respiratory mask comprises a seal. The seal comprises a gas inlet and is configured to seal against the user's face, and a mask housing directly or indirectly attached to the seal. The mask housing comprises at least one gas inlet. At least a portion of the mask housing may be formed from a fabric. The mask housing is configured to be of a substantially compliant 3-dimensional shape so as to deform under a sufficient external force without breaking the seal between the mask interface and the user's face and to be substantially resilient so that, after the external force is removed, the mask housing can at least partially revert to its original 3-dimensional shape either with or without user assistance.

In a second aspect, the invention provides a respiratory mask comprising a mask interface according to the first aspect of the invention and further comprising headgear for holding the mask interface against a user's face. Optionally, the headgear comprises a pair of collapsible gas delivery conduits configured to deliver gas from a gas source to the gas inlet(s) of the mask housing. The gas delivery conduits may be at least partially formed from a textile. Optionally, the gas delivery conduits are configured to connect to a gas delivery tube of a respiratory system at the top of the headgear.

In a third aspect, the invention provides a respiratory system comprising a respiratory mask according to the second aspect of the invention and a gas delivery tube comprising a first end configured to connect to the mask interface and a second end configured to connect to a gas source. Optionally, the respiratory system is configured for use with a CPAP machine.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Throughout this specification and claims, the term "textile layer" is intended to mean a layer of the mask housing that at least partially comprises a textile/fabric.

Terms such as "top", "bottom', "upper", "lower", "front", "back", "left", "right", "rear", and "side" describe the orientation and/or location of portions of the components or elements within a consistent but arbitrary frame of reference which is made clear by reference to the text and the associated drawings describing the components or elements under discussion. Moreover, terms such as "first", "second", "third", and so on may be used to describe separate components. Such terminology may include the words specifically mentioned above, derivatives thereof, and words of similar import.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

BRIEF DESCRIPTION OF THE DRAWINGS

Preferred forms of the invention will now be described in relation to the accompanying drawings in which.

DETAILED DESCRIPTION

Figure 1:
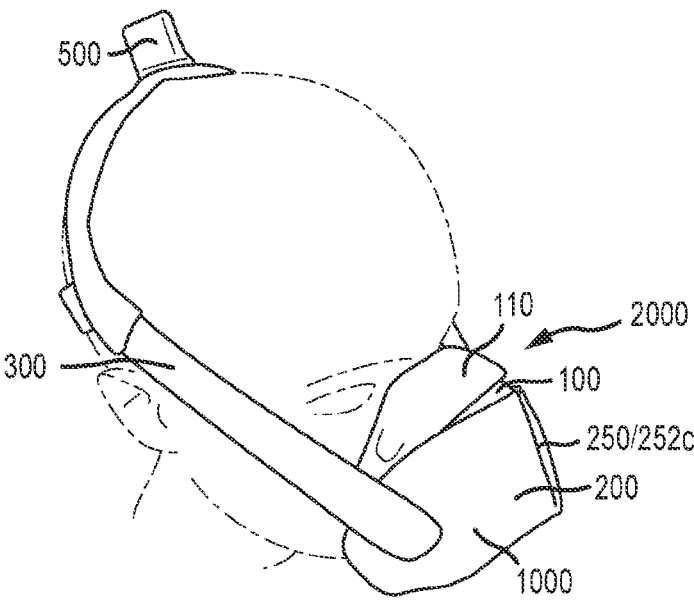
FIG. 1 is a perspective view of one form of mask interface according to the present invention.

Referring to FIGS. 1 to 9, the invention relates to a mask interface 1000, a respiratory mask 2000 comprising such a mask interface 1000, and a respiratory system for the delivery of breathing gas to a user. The respiratory mask 2000 is configured to be worn by a user to deliver breathing gas to the user. The respiratory mask 2000 comprises a mask interface 1000, comprising a seal 100 and mask housing 200, and a headgear assembly 300. Optionally, the mask interface 1000 also comprises a frame 400 that supports the seal 100 and mask housing 200. The respiratory mask 2000 may be a full face mask, a nasal mask or a pillows mask.

The mask interface 1000 may comprise a connection system to attach to the headgear assembly 300. The headgear assembly 300 is used to hold the mask interface 1000 to the user's face. The headgear is typically attached to the mask interface 1000 and wraps around the rear of the user's head to seal the mask interface 1000 against the user's face. Various forms of connection systems may be used to attach the headgear assembly 300 to the mask interface 1000. Similarly, the mask interface 1000 may be coupled to at least one and possibly multiple different types of headgear assemblies 300.

The seal 100 of the mask interface may comprise a front or distal surface and a rear surface or proximal surface. The rear surface of the seal 100 may be configured to substantially seal against a user's face during use. The seal 100 may be configured to fit over a user's mouth, nose, or both for sealing around and/or underneath a user's mouth and/or nose.

In one form, as shown particularly in FIGS. 1 to 5, the seal 100 forms a mask cushion configured to contact a user's face and to form a seal between the user's face and the mask interface 1000. For example, the seal 100 may be configured to substantially seal around a user's nose and mouth. Optionally, the seal 100 is resiliently deformable to fit and seal against a range of facial geometries. In one form, the seal 100 may comprise a rolling bridge 110 that fits over a user's nose and provides the seal 100 with a degree of customization to better fit and seal with a user's face. The seal 100 may be formed of any suitable material, such as silicone for example.

The seal 100 may comprise a gas inlet opening for receiving a breathing gas.

The mask housing 200 may be at least partially formed, and preferably fully formed, from a fabric/textile formed into a 3-dimensional shape. The fabric mask housing 200 may be substantially deformable under a sufficient external force. The mask housing 200 may also be configured to resume its original 3-dimensional shape either automatically after removal of the external force, or by manipulation of the mask housing 200 by a user. For example, the fabric mask housing 200 may comprise a first support structure/structural support 250 that is substantially flexible, to allow the mask housing to at least partially deform under a sufficient external force, and that is substantially resilient, to allow the mask housing 200 to substantially revert to its original 3-dimensional shape after removal of the external force.

Figure 6:
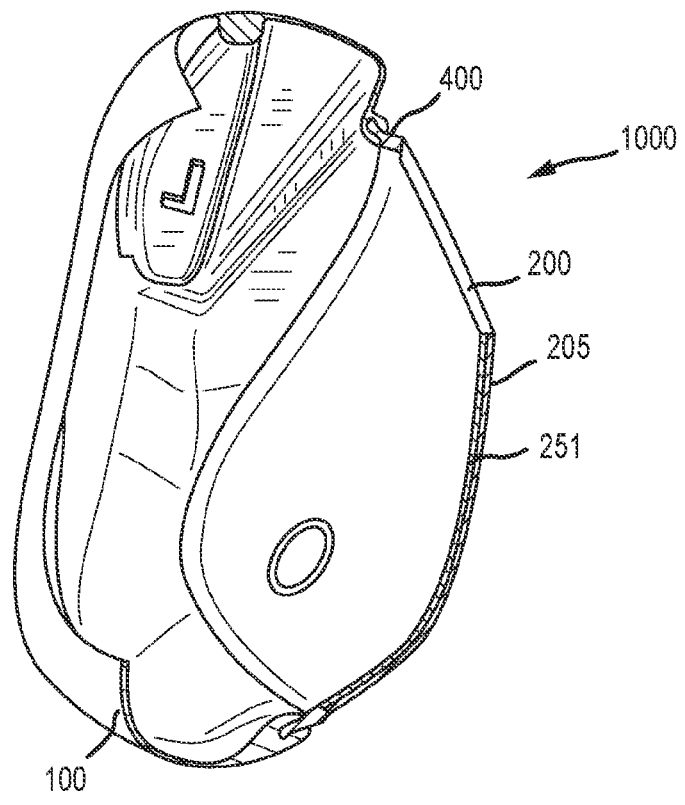
FIG. 6 is a partial cut-away side view of one form of mask showing a gas inlet at the side of the mask.
Figure 7:
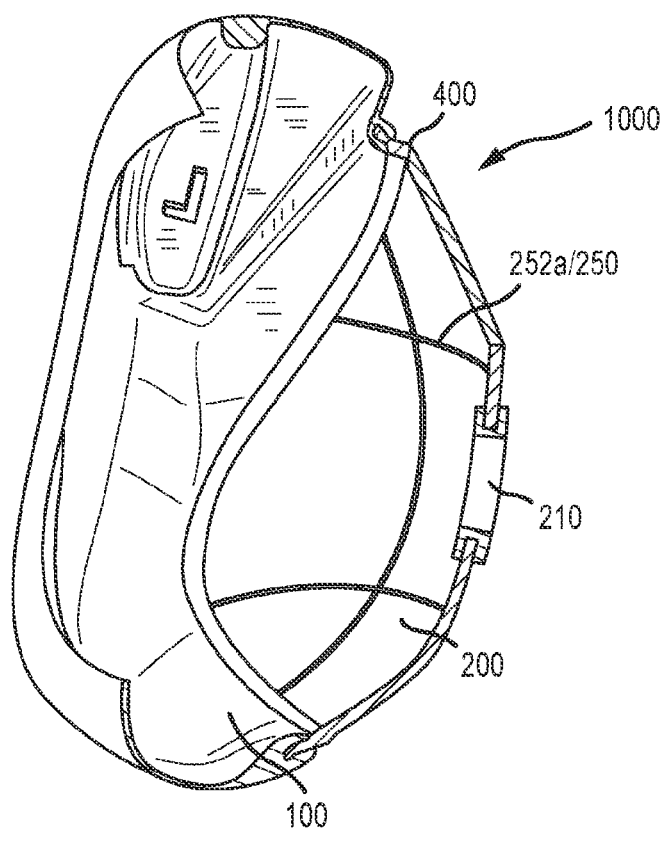
FIG. 7 is a partial cut-away side perspective view of another form of mask showing a support structure for a mask housing that includes support members in the form of filaments.

In embodiments, such as those shown in FIGS. 6 and 7, where the mask interface 1000 comprises a frame 400, the seal 100 is configured to be attached to the frame 400. Optionally, the seal 100 comprises one or more attachment features to help locate and/or attach the seal 100 to the frame 400. In one form, the seal 100 may be over-moulded to the frame 400.

The frame 400 may be configured to provide additional structure to the seal 100. For example, the frame 400 may comprise a substantially resilient structure to prevent the seal 100 from collapsing unintentionally. The frame 400 may also provide additional structure to the deformable fabric mask housing 200. For example, the frame 400 may provide a support structure/structural support 450 to the mask housing 200. Where the mask housing 200 includes a first support structure 250, the frame 400 may optionally provide a second support structure. Alternatively, the frame 400 may provide the only support structure for the mask housing 200. In yet another form, only the mask housing 200 may comprise a support structure to support its 3-dimensional shape.

The frame 400 may comprise a body comprising a first surface or front surface and a substantially opposing second surface or rear surface. The body of the frame 400 may comprise an outer edge that defines the outer periphery of the frame 400. The frame 400 also comprises a gas inlet that may be located substantially centrally within the frame. The gas inlet is defined by an inner edge of the frame 400 and may be relatively large so that the body of the frame 400 forms a substantially thin boundary structure around the gas inlet. For example, the frame 400 may comprise a ring-like support structure for supporting the seal 100 and mask housing 200. The ring-like support structure of the frame 400 may be of any suitable regular or irregular shape, such as a substantially circular or elliptical shape, an oval shape, a triangular shape or a quadrilateral shape for example.

The frame 400 and seal 100 may be configured to be attached together so that the gas inlet openings of each part substantially align with each other. In one form, the frame 400 may comprise a gas inlet opening defined by a substantially continuous edge provided by a seal flange projecting from the rear surface of the frame 400. The gas inlet opening 120 of the seal 100 may comprise a substantially continuous lip configured to attach to the seal flange of the frame 400.

The frame 400 is typically located at or near an outer peripheral edge of the mask housing 200 and is configured to provide a substantially rigid connection by which the mask housing 200 may be connected to the seal 100. For this reason, the frame 400 is preferably made from a material that has greater rigidity than the seal 100 and mask housing 200 so that the frame 400 is capable of providing sufficient support to the seal 100 and housing 200. In one form, the frame 400 is made from polycarbonate, but in alternative forms, the frame may be made from any suitable rigid or semi-rigid material, such as nylon, polypropylene, other rigid or semi-rigid plastics, or even metal. In another embodiment, the frame 400 may comprise a thickened rim of material, such as silicone, on the outer perimeter of the seal 100. The resilient configuration of the frame 400 may provide the mask interface 1000 with a support structure to support the seal and/or mask housing.

In one form, the frame may be over-moulded to the mask housing 200. In another form, the mask interface 1000 may comprise a clipping structure that connects the seal 100, frame 400 and housing 200 together. However, it should be appreciated that any other suitable attachment system may be used to attach the seal 100, housing 200 and frame 400 together.

The mask housing 200 may be configured to provide at least one gas inlet 210 that substantially forms a fluid flow path with the gas inlets of the seal 100 and frame 400 to provide the mask interface 1000 with a gas inlet. Optionally, the mask housing 200 comprises a pair of gas inlets 210 configured to form a fluid flow path with the gas inlets of the seal 100 and frame 400 and to connect to a pair of gas supply conduits 350 (350a and 350b). The gas inlet(s) 210 may be located at one or both sides of the mask housing 200, as shown in FIG. 6, or at the front of the mask housing 200, as shown in FIG. 7.

The mask housing 200 may be at least partially or entirely formed of fabric and may be configured to provide an appearance of softness and comfort. The fabric may be any suitable form of woven or knitted textile/fabric and may comprise natural fibres (such as cotton, wool, or bamboo fibres, for example), synthetic fibres (such as nylon, poly-propylene, or acrylic fibres, for example) or a combination of both. Preferably, at least an outer surface of the mask housing 200 comprises a soft, non-scratchy fabric.

The mask housing 200 may be configured to provide a flexible but substantially resilient enclosure that directly or indirectly attaches to the seal 100 to form an airtight breathing chamber.

To ensure that the mask housing 200 is airtight, the fabric used in the housing 200 should be airtight or should be used in combination with an airtight material, such as vinyl for example. In one form, at least the fabric portion of an inner surface of the housing 200 may comprise a layer or coating of airtight material. In another form, the fabric portion of the housing 200 may be impregnated with a substance such as plastic or resin that provides the fabric/textile with airtight properties.

Figure 4:
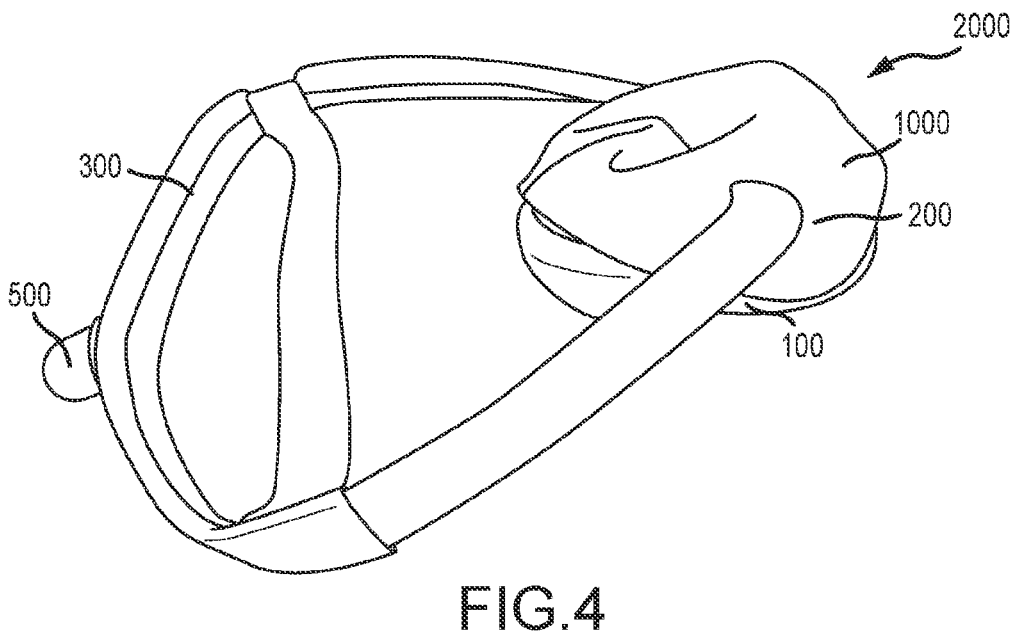
FIG. 4 is a perspective top view of the mask interface of FIG. 1 in a collapsed or deformed state.

In one form, the mask housing 200 may be configured to be sufficiently flexible to at least partially collapse under an external force, such as when pressed against a pillow for example. FIG. 4 illustrates one form of respiratory mask 2000 in which the mask housing 200 has been deformed. In this embodiment, the collapsing mask housing 200 reduces mask pull when the mask interface 1000 presses against the pillow or bed so that a user may sleep comfortably on his or her side while wearing the respiratory mask 2000. The mask housing 200 may also be configured so that the seal against a user's face is substantially retained even when the mask housing 200 partially collapses or when the user wears the mask interface 1000 while sleeping on his or her side.

The mask housing 200 of the present invention may be configured to be substantially resilient. For example, the mask housing 200 may be configured to have a shape memory so that a user can manipulate a collapsed mask to substantially return the mask to its original non-collapsed 3-dimensional shape. In some forms, the mask housing 200 may be configured to provide a shape memory that biases the mask housing 200 to a non-collapsed 3-dimensional shape. In this embodiment, after removing the external force that has caused the mask housing 200 to collapse, the mask housing 200 may automatically return to or substantially return to its non-collapsed shape without interference from a user.

In one form, the mask housing 200 may be configured to be sufficiently resilient to return to a substantially non-collapsed 3-dimensional shape by using a first support structure 250. The first support structure 250 may interact with at least the fabric portion of the mask housing 200 to encourage the housing 200 to return to its original shape after the housing 200 has been deformed under an external force.

Figure 5:
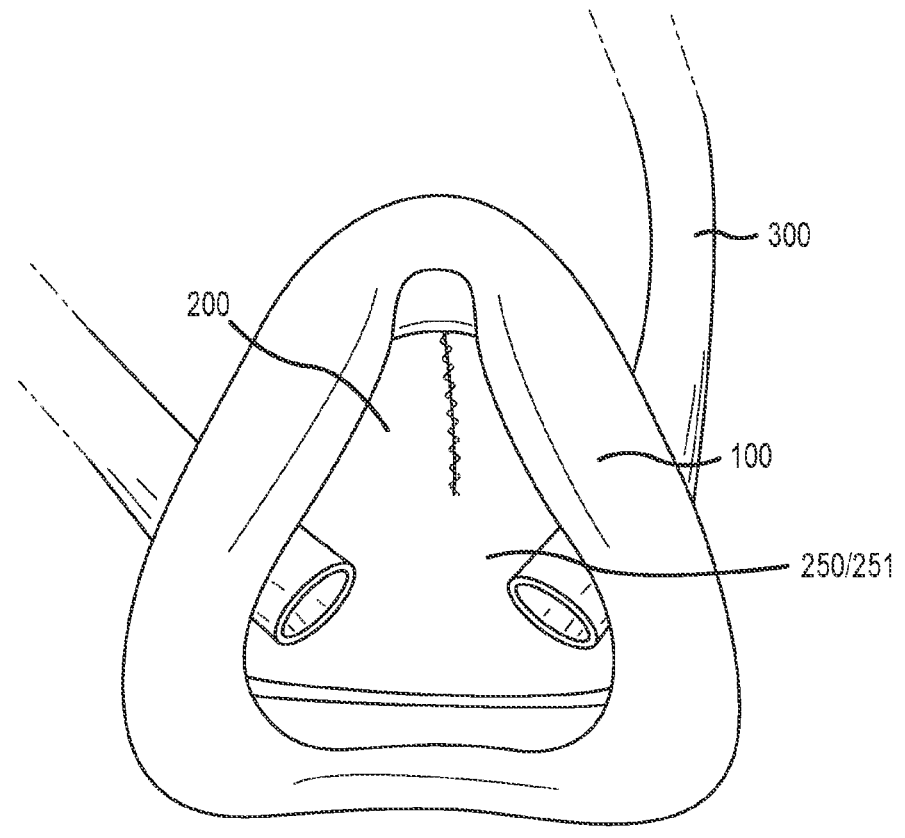
FIG. 5 is a rear view of one form of mask interface showing a support structure for a mask housing that includes a substantially resilient layer of material.

In one form, as shown in FIGS. 5 and 6, the mask housing 200 may comprise the first support structure 250 in the form of a support layer 251 configured to provide additional structure to the mask interface 1000. In one form, the support layer 251 may be a resilient layer comprising an elastomer, such as silicone for example, that is applied to the interior and/or exterior of at least one fabric portion 205 of the mask housing 200. The resilient support layer may be applied to one or more regions of the mask housing 200 to increase the thickness of those regions. In one form, as shown in FIG. 6, the support layer 251 may be an interior lining or coating. For example, the support layer 251 may be a vinyl or silicone lining. The interior lining may be configured to be thicker in areas of the mask housing 200 where additional structure is required. For example, the interior lining may be thicker near outer edges of the mask housing 200 and/or along sides of the mask housing 200.

The support members 252 may or may not interconnect with each other. By interconnecting the support members 252, a more resilient first support structure 250 is provided to the mask housing. The geometry of the support members 252 may provide flexibility to allow the support members 252 to deform together with the mask housing 200.

The support members 252 may or may not interconnect with each other. By interconnecting the support members 252, a more resilient support structure 250 is provided to the mask housing. The geometry of the support members 252 may provide flexibility to allow the support members 252 to deform together with the mask housing 200.

In one form, as shown in FIG. 7, the support members 252 comprise resilient or semi-resilient filaments, such as plastic filaments or metal wires for example. The filaments 252a may be configured to at least partially deform under force, such as under an external pressure force that occurs when the mask housing 200 presses against a pillow. The resilient nature of the filaments 252a means that the filaments 252a may be configured to automatically return to an original desired shape or to return to the original shape under manipulation by a user.

Figure 8:
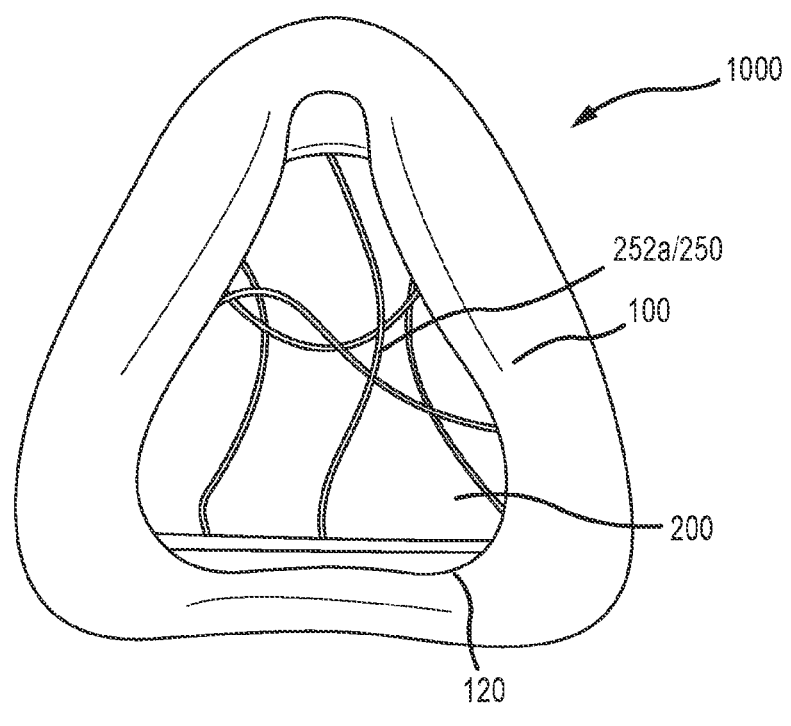
FIG. 8 is a rear view of the mask of FIG. 7.

In one form, as shown in FIG. 8, the support members 252 may be located on an interior surface of the fabric/textile layer of the mask housing to form an internal skeleton first support structure 250 that may or may not be connected to the fabric layer. In another form, the support members 252 may be integrally formed with a fabric layer to form the mask housing 200. For example, the support members 252 may comprise a plastic or silicone material and may be co-moulded with fabric to form the mask housing 200. In yet another form, the support members 252 may be located on an exterior surface of the mask housing 200 and may be attached to the mask housing 200 to provide structural support.

Figure 9:
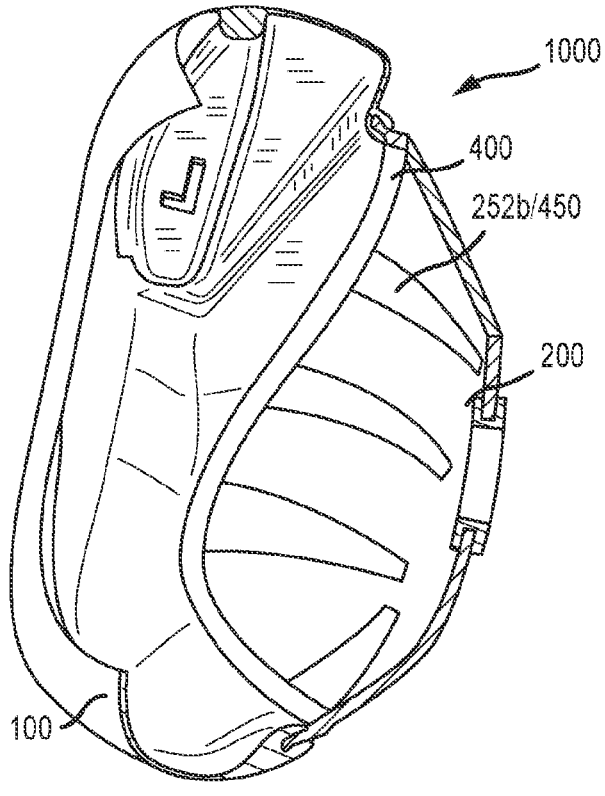
FIG. 9 is a partial cut-away side perspective view of another form of mask having a frame and a support structure comprising support fingers that extend from the frame to support the 3-dimensional shape of the mask housing.

In another form, as shown in FIG. 9, the support members 252 comprise fingers 252b that extend from the frame 400 of the mask interface 1000, forming a support structure 450 of the frame 400. Optionally, the fingers 252b may be made from the same material as the frame 400. In one form, the fingers 252b are integral with the mask housing 200. For example, the fingers 252b may be co-moulded with the mask housing 200.

Figure 3:
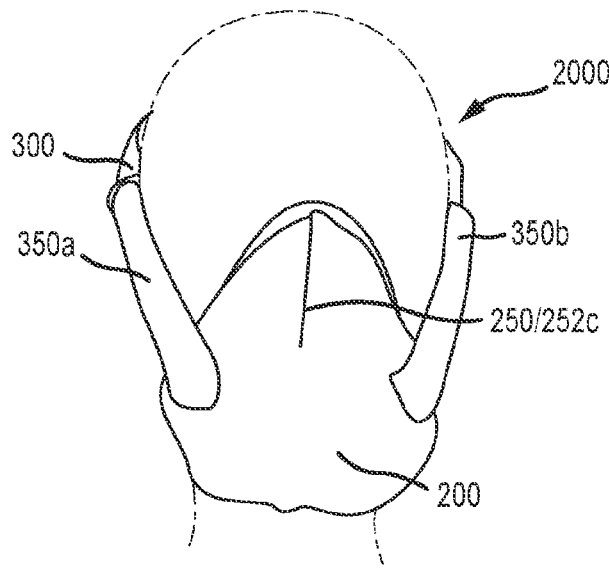
FIG. 3 is a front view of the mask interface of FIG. 1.

In another form, as shown in FIG. 3, the mask housing 200 may comprise a first support structure 250 in the form of a ridge 252c that is provided in a fabric/textile portion of the housing 200. The ridge 252c may form a fold line along which the mask housing 200 will naturally fold when squashed. The ridge 252c may be configured to provide the mask housing 200 with sufficient support to hold a three-dimensional shape and to at least partially collapse under force. The ridge 252c may be a fold (such as a pleat for example) or seam formed in the mask housing 200. Optionally, the ridge 252c extends from a substantially central point at a central region of the mask housing 200 to a substantially central point near an upper edge of the mask housing 200. In this configuration, the ridge 252c may form a substantially vertical line.

In one form, as shown best in FIG. 3, the mask housing 200 is formed from a single sheet of fabric/textile that is formed into a 3-dimensional shape by at least one seam that forms a ridge 252c along which the housing will naturally fold when squashed. The seam or ridge 252c forms a first support structure 250 that provides additional structure and some resilience to the housing 200. In another form, the 3-dimensional shape of the resilient mask housing 200 may be formed from multiple pieces of fabric joined by one or more seams to form one or more fold lines or ridges 252c to form a support structure. In both of these configurations, the seams in the fabric layer may provide the mask housing with an element of structural resilience and may help a user to manipulate a collapsed mask interface 1000 so as to return the mask interface 1000 to a substantially non-collapsed state.

An additional or alternative way of configuring the mask housing 200 to provide a shape memory may be by selecting a fabric that encourages the mask housing 200 to at least partially collapse under force and to substantially return to a non-collapsed form either automatically or by manipulation from a user.

In one form, the mask interface 1000 may comprise a seal 100, as described above, and a mask housing 200, as described above. In other words, it is not essential for the mask interface 1000 to comprise a frame 400. In this form, the seal 100 and mask housing 200 may be configured to connect to each other by any suitable attachment system. For example, the seal 100 and housing 200 may comprise complimentary attachment features, such as male and female attachment members or a clipping structure, as described above. In another form, the seal 100 and housing 200 may be adhered together or the seal 100 may be over-moulded to the housing 200. In yet another form, the seal 100 may comprise a lip or channel that engages with an edge of the mask housing 200 to attach the housing 200 to the seal 100.

Figure 2:
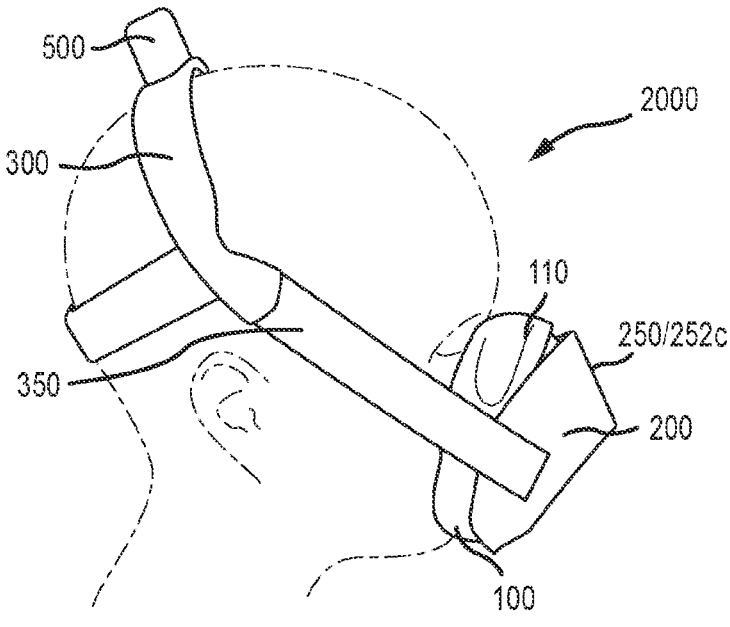
FIG. 2 is a side view of the mask interface of FIG. 1.

The respiratory mask 2000 is configured to connect to a supply of breathable gas to deliver breathable gas to a user via the mask interface 1000. In one form, the respiratory mask 2000 comprises a pair of collapsible gas supply conduits 350 that form part of a headgear assembly 300. The gas supply conduits 350 may be formed of any suitable material. For example, the gas supply conduits 350 may be at least partially or fully formed from fabric. In one form, the gas supply conduits 350 are formed from an airtight fabric/textile material. The gas supply conduits 350 are configured to extend across each side of a user's face, in use, as shown in FIGS. 1 to 3.

Optionally, the gas supply conduits 350 are configured to connect to a gas delivery tube of a respiratory system via a connection 500 at the top of the headgear assembly 300 so that in use, the connection 500 will be located at the top of the user's head. In this configuration, the effect of hose pull (from the gas delivery tube pulling on the respiratory mask) is reduced. In another form, the gas supply conduits 350 may be connected to the mask housing via traditional direct connections or elbow connections for example.

In one form, the respiratory mask 2000 or mask interface 1000 may be configured for use with a CPAP machine.

In one form, the respiratory mask 2000 may form part of a respiratory system that also comprises a gas delivery tube comprising a first end configured to connect to the mask interface 1000 and a second end configured to connect to a gas source.

The respiratory mask 2000, mask interface 1000 and respiratory system of the invention may provide several advantages. For example, the resilient mask housing 200 of the mask interface 1000 may be sufficiently compliant to suit the user's sleeping position without compromising sealing performance By using a silicone seal 100 with the mask interface 1000, a substantially reliable sealing structure may be provided that is also easy to fit.

In some forms, the fabric/component of the mask housing 200 may make the respiratory mask 2000 feel and/or look soft and warm to touch, which may provide the respiratory mask 2000 with a less clinical appearance and may be more comforting to a user.

The invention claimed is:

1. A mask interface configured to deliver breathing gas to a user, the mask interface comprising:

a seal comprising a gas inlet configured to seal against a face of the user; and a 3-dimensional mask housing directly or indirectly attached to the seal, wherein breathing gas within the 3-dimensional mask housing passes through the gas inlet of the seal to reach the user, wherein the 3-dimensional mask housing comprises:

at least one gas inlet opening that permits breathing gas to enter the 3-dimensional mask housing, at least one fabric portion, and a flexible, resilient support structure configured to at least partially retain a shape of the 3-dimensional mask housing, the flexible, resilient support structure comprising a plurality of support members each comprising a first end and a second end, wherein the second end of each of the plurality of support members is a free end;

wherein an airtight coating or layer is provided on an internal surface of the at least one fabric portion of the 3-dimensional mask housing in use such that the at least one fabric portion defines at least a portion of an airtight positive pressure chamber of the 3-dimensional mask housing.

2. The mask interface of claim 1, wherein the plurality of support members is integrally formed with the at least one fabric portion.

3. The mask interface of claim 1, wherein each of the plurality of support members interconnects with each other.

4. The mask interface of claim 1, wherein the flexible, resilient support structure comprises a skeleton structure comprising the plurality of support members.

5. The mask interface of claim 1, wherein a width of the first end is greater than a width of the second end.

6. The mask interface of claim 5, wherein each of the plurality of support members curves inwardly such that the second end of each of the plurality of support members is inwardly disposed relative to the first end.

7. The mask interface of claim 5, wherein each of the plurality of support members has a squared-off end at the second end.

8. The mask interface of claim 1, wherein each of the plurality of support members extends partially across the 3-dimensional mask housing.

9. The mask interface of claim 1, further comprising a frame comprising a gas inlet configured to receive breathing gases from the 3-dimensional mask housing and being configured to attach to the seal and the 3-dimensional mask housing so that the gas inlet of the frame, the gas inlet of the seal and the at least one gas inlet opening of the 3-dimensional mask housing each form a portion of a fluid flow path of breathing gas through the mask interface to the user.

10. The mask interface of claim 9, wherein the frame extends around a perimeter of the 3-dimensional mask housing and each of the plurality of support members is joined to the frame.

11. The mask interface of claim 9, wherein the plurality of support members is formed from a first material and the frame is formed from the first material.

12. The mask interface of claim 9, wherein the frame connects the 3-dimensional mask housing to the seal.

13. The mask interface of claim 1, wherein the seal is formed of silicone.

14. The mask interface of claim 1, wherein the flexible, resilient support structure of the 3-dimensional mask housing is configured to at least partially deform under a sufficient deforming external force and to substantially return to its original shape after the sufficient deforming external force is removed.

15. The mask interface of claim 1, wherein the flexible, resilient support structure is located on an interior surface of the at least one fabric portion of the 3-dimensional mask housing.

16. The mask interface of claim 1, wherein the flexible, resilient support structure comprises a resilient support layer applied to interior and/or exterior surfaces of the at least one fabric portion of the 3-dimensional mask housing to increase a thickness of one or more regions of the 3-dimensional mask housing.

17. The mask interface of claim 16, wherein the resilient support layer is applied near outer edges of the 3-dimensional mask housing and/or along sides of the 3-dimensional mask housing to increase the thickness of these regions of the 3-dimensional mask housing.

18. The mask interface of claim 16, wherein the resilient support layer comprises an elastomer.

19. The mask interface of claim 16, wherein the resilient support layer comprises a vinyl or silicone lining.

20. The mask interface of claim 1, wherein the flexible, resilient support structure comprises a ridge that is provided in the at least one fabric portion of the 3-dimensional mask housing.

21. The mask interface of claim 20, wherein the ridge comprises at least one fold line or seam.

22. The mask interface of claim 20, wherein the ridge extends from a substantially central point at a central region of the 3-dimensional mask housing to a substantially central point near an upper edge of the 3-dimensional mask housing.

23. The mask interface of claim 1, wherein the free end of each of the plurality of support members provides support to the at least one fabric portion of the 3-dimensional mask housing.

24. A respiratory system comprising:

a mask interface according to claim 1;

a breathing gas delivery tube comprising a first end configured to connect to the at least one gas inlet opening of the mask interface and a second end; and a CPAP machine configured to provide breathing gas, wherein the second end of the breathing gas delivery tube is configured to connect to the CPAP machine.

25. A mask interface configured to deliver breathing gas to a user, the mask interface comprising:

a seal comprising a gas inlet configured to seal against a face of the user; and a 3-dimensional mask housing directly or indirectly attached to the seal, wherein breathing gas within the 3-dimensional mask housing passes through the gas inlet of the seal to reach the user, wherein the 3-dimensional mask housing comprises:

at least one gas inlet opening that permits breathing gas to enter the 3-dimensional mask housing, at least one fabric portion that is configured to be airtight and form at least a portion of a positive pressure chamber of the 3-dimensional mask housing, and a flexible, resilient support structure configured to retain a shape of at least a portion of the 3-dimensional mask housing, the flexible, resilient support structure comprising a plurality of support members each comprising a first end and a second end, wherein the second end of each of the plurality of support members is a free end.

5

\* \* \* \* \*